United States Patent
Köhler

(10) Patent No.: US 10,406,384 B2
(45) Date of Patent: Sep. 10, 2019

(54) ACOUSTIC RADIATION FORCE MAGNETIC RESONANCE IMAGING

(71) Applicant: Profound Medical Inc., Mississauga (CA)

(72) Inventor: Max Oskar Köhler, Espoo (FI)

(73) Assignee: Profound Medical Inc., Mississauga, ON (CA)

( * ) Notice: Subject to any disclaimer, the term of this patent is extended or adjusted under 35 U.S.C. 154(b) by 1118 days.

(21) Appl. No.: 14/412,728

(22) PCT Filed: Jun. 28, 2013

(86) PCT No.: PCT/IB2013/055306
§ 371 (c)(1),
(2) Date: Jan. 5, 2015

(87) PCT Pub. No.: WO2014/009834
PCT Pub. Date: Jan. 16, 2014

(65) Prior Publication Data
US 2015/0190659 A1    Jul. 9, 2015

Related U.S. Application Data

(60) Provisional application No. 61/669,210, filed on Jul. 9, 2012.

(51) Int. Cl.
*A61N 7/02* (2006.01)
*A61B 5/055* (2006.01)
(Continued)

(52) U.S. Cl.
CPC .......... *A61N 7/02* (2013.01); *A61B 5/015* (2013.01); *A61B 5/055* (2013.01); *A61B 5/7278* (2013.01);
(Continued)

(58) Field of Classification Search
CPC ............... G01R 33/20; G01R 33/4804; G01R 33/4808; G01R 33/4814; G01R 33/56358; A61B 5/015; A61B 5/055; A61N 7/02
See application file for complete search history.

(56) References Cited

U.S. PATENT DOCUMENTS 6,650,118 B2    11/2003    Leussler
8,428,689 B2    4/2013    Kuhn et al.
(Continued)

FOREIGN PATENT DOCUMENTS

EP    0948929 A2    10/1999
JP    2003038459 A    2/2003
(Continued)

OTHER PUBLICATIONS

Kaye, Elena A., Jing Chen, and Kim Butts Pauly. "Rapid MR-ARFI method for focal spot localization during focused ultrasound therapy." Magnetic resonance in medicine 65, No. 3 (2011): 738-743.*
(Continued)

*Primary Examiner* — Carolyn A Pehlke
(74) *Attorney, Agent, or Firm* — Intrinsic Law Corp.

(57) ABSTRACT

The invention provides for medical instrument (200, 400) comprising a magnetic resonance imaging system (202) and a high intensity focused ultrasound system (222). A processor (246) controls the medical instrument. Instructions cause the processor to control (100) the magnetic resonance imaging system to acquire the magnetic resonance data using a pulse sequence (254). The pulse sequence comprises an acoustic radiation force imaging pulse sequence (500, 600). The acoustic radiation force imaging pulse sequence comprises an excitation pulse (512) and a multi-dimensional gradient pulse (514) applied during the radio frequency excitation pulse for selectively exciting a region of interest (239) encompassing a target zone and at least a portion of the beam axis. The instructions cause the processor to control (Continued)

(102) the high intensity focused ultrasound system to sonicate the target zone during the acoustic radiation force imaging pulse sequence and reconstruct (104) a radiation force image (258) using the magnetic resonance data.

20 Claims, 6 Drawing Sheets

(51) Int. Cl.
    *G01R 33/48*     (2006.01)
    *G01R 33/483*     (2006.01)
    *G01R 33/561*     (2006.01)
    *A61B 5/01*     (2006.01)
    *A61B 5/00*     (2006.01)
    *G01R 33/54*     (2006.01)
    *A61B 18/00*     (2006.01)
    *A61N 7/00*     (2006.01)
    *A61B 90/00*     (2016.01)

(52) U.S. Cl.
    CPC .......... *A61B 5/748* (2013.01); *G01R 33/4814* (2013.01); *G01R 33/4833* (2013.01); *G01R 33/543* (2013.01); *G01R 33/5611* (2013.01); A61B 2018/00791 (2013.01); A61B 2090/374 (2016.02); A61B 2505/05 (2013.01); A61N 2007/0039 (2013.01); G01R 33/5612 (2013.01)

(56) References Cited

U.S. PATENT DOCUMENTS

| | | | |
|---|---|---|---|
| 2002/0193681 A1* | 12/2002 | Vitek | G01R 33/28 600/411 |
| 2010/0049047 A1 | 2/2010 | Shin | |
| 2011/0080166 A1 | 4/2011 | Edelman et al. | |
| 2011/0248714 A1 | 10/2011 | Salomir | |
| 2011/0270075 A1 | 11/2011 | Vitek | |
| 2011/0270136 A1 | 11/2011 | Vitek | |

FOREIGN PATENT DOCUMENTS

| | | |
|---|---|---|
| JP | 2011504378 A | 2/2011 |
| WO | 02084308 A1 | 10/2002 |
| WO | 2012063162 A1 | 5/2012 |

OTHER PUBLICATIONS

Saritas, Emine Ulku, Charles H. Cunningham, Jin Hyung Lee, Eric T. Han, and Dwight G. Nishimura. "DWI of the spinal cord with reduced FOV single-shot EPI." Magnetic resonance in medicine 60, No. 2 (2008): 468-473.*
Ma, Chao, Dan Xu, Kevin F. King, and Zhi-Pei Liang. "Reduced field-of-view excitation using second-order gradients and spatial-spectral radiofrequency pulses." Magnetic resonance in medicine 69, No. 2 (2013): 503-508.*
McDannold et al "Magnetic Resonance Acoustic Radiation Force Imaging" Medical Physics, vol. 35, Aug. 2008.
Schneider et al "Inner-Volume Imaging in Vivo using Three-Dimensional Parallel Spatially Selective Excitation", Magnetic Resonance in Medicine, 2012.
Wilm, B.J. et al, "Reduced Field-of-View MRI using Outer Volume Suppression for Spinal Cord Diffusion Imaging" Magnetic Resonance in Medicine, vol. 57, No. 3. 2007 pp. 625-630.
Kaye, Elena A. et al "Adapting MRI Acoustic Radiation Force Imaging for in Vivo Human Brain Focused Ultrasound Applications", Magnetic Resonance in Medicine, vol. 69, No. 3, May 2012, pp. 725-728.
Kaye, Elena A. et al "Rapid MR-ARFI Method for Focal Spot Localization during Focused Ultrasound Treatments", AIP Conference Proceedings, Jan. 2010, pp. 247-250.
Carvajal Gallardo, Elma, "MR Methods for Imaging of Acoustic Radiation Force in Tissue", Oct. 2010, Utrecht University, Master Thesis.
Chen, J. et al "MR Acoustic Radiation Force Imaging: Comparison of Encoding Gradients", Proceedings International Society Magnetic Resonance in Medicine, vol. 16, 2008, pp. 1240.

* cited by examiner

ACOUSTIC RADIATION FORCE MAGNETIC RESONANCE IMAGING

CROSS-REFERENCE TO PRIOR APPLICATIONS

This application is the U.S. National Phase application under 35 U.S.C. § 371 of International Application No. PCT/IB2013/055306, filed on Jun. 28, 2013, which claims the benefit of U.S. Provisional Patent Application No. 61/669,201, filed on Jul. 9, 2012. These applications are hereby incorporated by reference herein.

TECHNICAL FIELD

The invention relates to magnetic resonance guided high intensity focused ultrasound, in particular it relates to the determination of tissue displacement by high intensity focused ultrasound using magnetic resonance imaging.

BACKGROUND OF THE INVENTION

In high intensity focused ultrasound (HIFU) an array of ultrasonic transducer elements are used to form an ultrasonic transducer. Supplying alternating current electrical power to the transducer elements causes them to generate ultrasonic waves. The ultrasonic waves from each of the transducer elements either add constructively or destructively at different locations in the beam path. By controlling the phase of alternating current electrical power supplied to each of the transducer elements the focal point or volume into which the ultrasound power is focused may be controlled.

High-intensity focused ultrasound (HIFU) therapy of tumors requires a high degree of spatial accuracy in order to avoid damaging healthy tissue as well as to obtain optimal usage of the system. Although avoiding damaging healthy tissue due to poor targeting is typically not a problem for large stationary tumors if utilizing low-power test sonications as is current practice, the technical performance and/or clinical performance of the system may suffer if incorrect positional knowledge is used for a feedback algorithm for example. This translates into reduced treatment efficiency.

Magnetic resonance (MR) acoustic radiation force imaging (MR-ARFI) may be used to observe the radiation force that mechanical pressure waves exert on in vivo tissue. This for example includes the estimation of the radiation force exerted by absorbed high-intensity focused ultrasound.

The journal article "Magnetic resonance acoustic radiation force imaging" by McDannold and Maier published in Medical Physics volume 35, August 2008, pages 3748 to 3758 discloses an elastographic method of determining the displacement cause by focused ultrasound using magnetic resonance imaging.

SUMMARY OF THE INVENTION

The invention provides for a medical instrument, a computer program product, and a method in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two or three dimensional data that has been acquired using a medical imaging scanner. A medical imaging scanner is defined herein as an apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

Magnetic resonance data may comprise the measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonance frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonance frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

Spectroscopic magnetic resonance data is defined herein as being the recorded measurements of radio frequency signals emitted by atomic spins by the antenna of a Magnetic resonance apparatus during a magnetic resonance imaging scan which contains information which is descriptive of multiple resonance peaks.

The spectroscopic magnetic resonance data may for instance be used to perform a proton spectroscopic (PS) imaging based temperature mapping method which can produce temperature maps on absolute scale. This absolute scale temperature map may therefore be used to perform a temperature calibration. This method relies on the physical principles of water proton resonance shift temperature dependence as the proton resonance frequency method, but the acquisition method is different: the frequency shift is calculated from the magnetic resonance spectra. The shift is calculated from the position difference of the water and a reference proton peak. Protons in lipids may for example be used as reference, as their resonance frequency is known to be almost independent of temperature, while the water proton peak has linear dependence on temperature. This can be done in the voxels, where both tissue types are present. If water and lipids do not exist in the same voxel, one may try to use some other tissue type than lipids as reference. If not successful, there may be some voxels where the reference peaks, and therefore the temperature data, are not available. Interpolation and/or temperature filtering may be used to help these situations, since body temperature is normally not expected to change rapidly spatially with the highly localized temperature rise typically caused by thermal therapy being an obvious exception. The utilization of reference peaks makes the method relatively independent of field drifts or inter-scan motion. Because the scanning takes a time of at least on the order of one minute with current methods, the PS method is susceptible to intra-scan motion or temperature change during scanning. In a case where temperature is constant or temperature variation is small both in time and space, the method is able to produce useful information. For example, with the Magnetic Resonance Guided High Intensity Focused Ultrasound (MR-HIFU), the PS method can be used to provide the actual body temperature distribution before start of MR-HIFU or other temperature treatment as opposed to using a spatially homogeneous starting temperature taken as the body core temperature measured with a thermometer probe. Alternatively, the PS method can be used as a sanity check for the cumulative temperature between heat treatments. This method can also be used as calibration at given time points during hyperthermia in order to reduce/remove phase artifacts due to for example main field drift or motion that are accumulated during PRF thermometry.

An 'ultrasound window' as used herein encompasses a window which is effectively transparent to ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical instrument comprising a magnetic resonance imaging system. The magnetic resonance imaging system is operable for acquiring magnetic resonance data from a subject within an imaging zone. The medical instrument further comprises a high-intensity focused ultrasound system for directing ultrasound along a beam axis for sonicating a target zone. The target zone is within the imaging zone. The medical instrument further comprises a processor to control the medical instrument. The medical instrument further comprises a memory for storing machine-readable instructions. Execution of the machine-readable instructions causes the processor to control the magnetic resonance imaging system to acquire the magnetic resonance data using a pulse sequence. A pulse sequence as used herein is a set of commands or controls which sequentially control the operation of the magnetic resonance imaging system for the acquisition of magnetic resonance data. The pulse sequence comprises an acoustic radiation force imaging pulse sequence. It is understood as used herein that a pulse sequence may also refer to a combination or interleaving of various pulse sequences. The acoustic radiation force imaging pulse sequence comprises an excitation pulse. The acoustic radiation force imaging pulse sequence further comprises a multi-dimensional gradient pulse or waveform applied during the radio-frequency excitation pulse for selectively exciting a region of interest.

A multi-dimensional gradient pulse or waveform as used herein encompasses a gradient pulse or waveform which comprises at least two time-varying spatial components in perpendicular directions. Transmit k-space is consequently traversed in at least two dimensions when applying the radio-frequency excitation pulse in conjunction with the multi-dimensional gradient waveform. A circular transmit k-space trajectory can for example be achieved by sinusoidal gradient waveforms applied in the x- and y-direction. The multi-dimensional transmit k-space trajectory causes the excited region of interest to be restricted in more than one direction. The spatial components of the multi-dimensional gradient do not need to be applied simultaneously in time although they often are, but can be applied successively. The radio-frequency excitation pulse may be a pulse train compromised of several radio-frequency excitation pulses slightly separated in time with zero radio-frequency power being applied in between. In many applications the several radio-frequency excitation pulses are separated by 5 ms or less in time.

The region of interest comprises a predetermined volume that encompasses the target zone and at least a portion of the beam axis. Execution of the instructions further causes the processor to control the high-intensity focused ultrasound system to sonicate the target zone using the high-intensity focused ultrasound system such that the sonication of the target zone occurs during the acoustic radiation force imaging pulse sequence. Execution of the instructions further cause the processor to reconstruct a radiation force image using the magnetic resonance data. This embodiment may be beneficial because the multi-dimensional gradient pulse limits the size of the region of interest. The reduced size of the region of interest may greatly reduce the time necessary to construct a radiation force image. This may enable real time control of the medical instrument using the radiation force image.

Embodiments of the invention may accelerate MR-ARFI such that the technique may become useful for a number of issues all primarily related to the direct estimation of in vivo pressure field. This estimate is useful in for example optimizing the heating efficiency and accuracy by maximizing the output pressure in the desired location for any set output power from the transducer (by altering the driving phases of the transducer elements and also for verifying the focal spot position, all without causing any notable heating or damage to the tissue itself. Moreover, MR-ARFI may also be used for monitoring the incidence of cavitation and non-linearities as the local absorption then suddenly changes thereby changing the local exerted radiation force. Finally, monitoring of pressure for gene delivery and drug delivery can also be used. These applications are all known, but little attention has been paid so far to optimize the MR techniques. While the use of MR-ARFI for test shot purposes is not time critical, the use of MR-ARFI for most other intentions are. Moreover, the insight that one typically is interested in only alterations in the estimated pressure when varying some parameter, not so much in exact high-resolution displacement maps, allows use of 1D readouts and reduced FOV imaging among other techniques to speed up acquisition.

In some embodiments the predetermined volume is much smaller than the imaging zone. In some embodiments the predetermined volume is 1/10 of the volume of the imaging zone. In other embodiments the predetermined volume is 1/100 of the volume of the imaging zone.

In some embodiments the spatial encoding performed during the acoustic radiation force imaging pulse sequence is done during displacement of the tissue by the high-intensity focused ultrasound system beam after the pulse from the ultrasound system is finished the tissue then relaxes back into place before the data is read out.

The use multi-dimensional gradient pulses for the selection of a three-dimensional region of interest has for example been detailed in the journal article Schneider et. al. (2012), Inner-volume imaging in vivo using three-dimensional parallel spatially selective excitation. Magn. Reson. Med. doi: 10.1002/mrm.24381. In this article spatially selective excitation in more than one dimension is achieved by playing out gradient waveforms in multiple spatial directions simultaneously to RF excitation. Two different three-dimensional transmit k-space trajectories are detailed therein: one being a stack of spirals k-space trajectory and the other being a concentric spherical shell k-space trajectory. The stack of spirals trajectory compromises an x and y-gradient component that are sinusoidal and the resulting k-space xy-plane spirals are separated by blip gradients in the z-direction. The concentric spherical shell trajectory is achieved by encoding spirals along the surface of spherical shells with altering radius. In the concentric shell trajectory the x and y-gradient components are similarly sinusoidal although with a radius depending on the z-component. The z-gradient has in turn constant amplitude during the encoding of each shell, then changing amplitude for encoding the next shell. Parallel transmission techniques were used in this study to undersample the transmit k-space, thereby shortening the total excitation duration.

In another embodiment the multi-dimensional gradient pulse is a two-dimensional gradient pulse for exciting the region of interest such that the region of interest has a two-dimensional cross-section. This may for example be achieved by playing out a sinusoidal gradient waveform with linearly increasing or decreasing amplitude during excitation in two spatial directions. The resulting transmit k-space trajectory is then a two-dimensional inward or outward progressing spiral depending on whether the gradient amplitude was decreasing or increasing, respectively. A spiral transmit k-space trajectory coupled with an RF pulse will result in a cylindrical so-called pencil beam excitation volume with a circular cross-section. Playing out different gradient waveforms in the two spatial directions will result in different volume excitations. The two-dimensional cross-section has a rotational symmetry with respect to a region of interest axis. The region of interest axis and the HIFU beam axis can be coaxial. Essentially the multi-dimensional gradients are used to control the shape of the region of interest. In some embodiments the two-dimensional cross-section is perpendicular to the region of interest axis. The rotational symmetry may have different forms. For some instances the rotation may be a rotation by a particular angle, for instance if any angle has the same symmetry then the cross-section is circular. The cross-section may also have a rectangular, triangular or polygonal or other shape which when rotated by a specific number of degrees is identical. This of course is excluding the case where the two-dimensional cross-section is rotated 360 degrees.

In another embodiment the two-dimensional excited volume has any one of the following: a circular cross-section, an elliptical cross-section, a rectangular cross-section and a polygonal cross-section.

In another embodiment the imaging pulse sequence further comprises a one-dimensional readout gradient pulse aligned with the beam axis. This is particularly beneficial when using a two dimensional excitation volume as outlined above. In this case the spatial direction of the two-dimensional gradients can advantageously be chosen perpendicular to the HIFU beam axis, which will result in an excitation volume that is spatially limited in the dimensions perpendicular to the HIFU beam axis. Applying a one-dimensional readout gradient along the HIFU beam axis will then cause all excited magnetization at each location perpendicularly to the beam axis to be displayed as projected onto the beam axis. If the region of interest that is excited by the multi-dimensional excitation is made sufficiently small around the beam axis then this projected one-dimensional readout may be used to obtain an accurate value for displacement of the tissue caused by the high-intensity focused ultrasound system. This may have the advantage of further speeding the acquisition of the data.

In another embodiment the magnetic resonance imaging system comprises a multi-element transmit coil. The pulse sequence is operable for causing the magnetic resonance imaging system to shorten the duration required for restricting the region of interest to a predetermined volume using the multi-element transmit coil. This embodiment may have the advantage of further reducing the time needed for limiting the size of the region of interest. Similarly, the reduction in time may be traded in for an improved spatial excitation profile. The multi-transmit coil enables undersampling of excitation k-space much in the same way as a receive coil array allows SENSE or undersampling of the receive k-space to shorten the acquisition by requiring less phase encodings.

In another embodiment the pulse sequence is a SENSE pulse sequence or a GRAPPA pulse sequence.

In another embodiment the medical instrument uses a motion encoding gradient that is a bi-polar gradient pulse. In this embodiment the sonication may be performed twice and the polarity of the motion encoding gradient is reversed. This is similar to the technique used in echo-planar imaging for reducing the effect of magnetic field inhomogeneities. The two phase images may then be subtracted to remove the background phase, while simultaneously obtaining a phase image with an average of two samples that only contains the ARFI displacement. This is beneficial compared to the approach of acquiring a separate ARFI image with no HIFU to remove the background phase, as the displacement encoded ARFI image is averaged (N=2) and a resulting improved SNR is obtained at no additional scan time.

In another embodiment execution of the instructions further causes the processor to perform any one of the following using the radiation force image: detect bubbles, detect tissue necrosis, determine tissue displacement, adjust target position, and combinations thereof.

In another embodiment execution of the instructions further causes the processor to perform drive signal optimization for the high intensity focused ultrasound system using the radiation force image. By measuring the displacement caused by the ultrasound beam, the level of ultrasound generated by the high intensity focused ultrasound system may be optimized or adjusted.

In another embodiment the excitation pulse is a single excitation pulse. What is meant by this is that the excitation and the multi-dimensional gradient pulse are formed as a single group of actions at a particular window of time. This is opposed to other excitation pulses that are divided into two parts, for instance when a 90 degree and a 180 degree pulse are used.

In another embodiment the pulse sequence further comprises a displacement encoding gradient pulse.

In another embodiment execution of the instructions further causes the processor to control the high-intensity focused ultrasound system to sonicate the target zone using the high-intensity focused ultrasound system such that the sonication of the target zone occurs during at least a portion of the displacement encoding gradient pulse.

In another embodiment the pulse sequence further comprises an outer volume suppression pulse sequence for attenuating the magnetic resonance signal outside of the region of interest. This may be achieved by applying a radio frequency pulse during the application of one-dimensional or two-dimensional gradients in a preparation step in order to tip down the magnetization in the regions to be suppressed. This is then followed by spoiler gradients to dephase the tipped down magnetization. Pulse trains using tip down and tip back pulses can be used before the spoiler gradients to create more complex suppression volumes such as a cylindrical suppression volume with a non-suppressed center. By applying a one-dimensional excitation pulse along the cylinder axis following the result will be a very similar excited volume of interest as that of a multi-dimensional pencil beam cylindrical excitation outlined earlier. This embodiment may be beneficial because it may further reduce the signal coming from outside a region of interest. A magnetization preparation sequence that attenuates signal outside of the region of interest may for example be used. This for instance may be performed before the multi-dimensional excitation pulse. In an alternative what may be performed is that the region outside of the region of interest is all suppressed using the outer volume suppression pulse sequence. Then a one-dimensional excitation may be used for exciting the region of interest. This method may be used to restrict the region that needs to be sampled much in the same way as multidimensional excitation does. Acquisition can be performed more rapidly of small volumes in this embodiment, due to the smaller volume needed to be sampled.

In another embodiment the pulse sequence comprises a thermal imaging pulse sequence for acquiring thermal magnetic resonance data. The thermal imaging pulse sequence is interleaved with the acoustic radiation force imaging pulse sequence. Execution of the instructions further causes the processor to control the magnetic resonance imaging system to acquire the thermal magnetic resonance data using the thermal imaging pulse sequence. Execution of the instructions further causes the processor to reconstruct a thermal map using the thermal magnetic resonance data. Execution of the instructions further cause the processor to display the thermal map and the radiation force image on a display.

In another embodiment the high-intensity focused ultrasound system has an adjustable focus for controlling the location of the target zone. Execution of the instructions further cause the processor to receive a treatment plan specifying a location of the target zone within the subject. Execution of the instructions further cause the processor to control the high-intensity focused ultrasound system to repeatedly control the adjustable focus at least partially in accordance with the radiation force image and the treatment plan in real time. This embodiment may have the advantage that the radiation force image is produced so rapidly that it may be used in real time. Using this in conjunction with the treatment plan the subject may be sonicated more efficiently.

In another embodiment the pulse sequence comprises an image pulse sequence for acquiring image magnetic resonance data. Execution of the instructions further causes the processor to repeatedly acquire the image magnetic resonance data. Execution of the instructions further causes the processor to repeatedly reconstruct an image using the image magnetic resonance data. Execution of the instructions further causes the processor to repeatedly determine the location using the image. The adjustable focus is controlled and of course at least partially using the location.

In another aspect the invention provides for a computer program product comprising machine-executable code for execution by a processor controlling the medical instrument. The medical instrument comprises a magnetic resonance imaging system for acquiring magnetic resonance data from a subject within an imaging zone. The medical instrument further comprises a high-intensity focused ultrasound system for directing ultrasound along a beam axis for sonicating a target zone. The target zone is within the imaging zone. Execution of the instructions further cause the processor to control the magnetic resonance imaging system to acquire the magnetic resonance data using the pulse sequence. The pulse sequence comprises an acoustic radiation force imaging pulse sequence. The acoustic radiation force imaging pulse sequence comprises an excitation pulse. The acoustic radiation force imaging pulse sequence comprises a multi-dimensional gradient pulse applied during the radio-frequency excitation pulse for selectively exciting a region of interest. The region of interest comprises a predetermined volume that encompasses the target zone and at least a portion of the beam axis. Execution of the instructions further causes the processor to control the high-intensity focused ultrasound system to sonicate the target zone using the high-intensity focused ultrasound system such that the sonication of the target zone occurs during the acoustic radiation force imaging pulse sequence. Execution of the instructions further cause the processor to reconstruct a radiation force image using the magnetic resonance data.

In another aspect the invention provides for a method of operating the medical instrument. The medical instrument comprises a magnetic resonance imaging system for acquiring magnetic resonance data from a subject within an imaging zone. The medical instrument further comprises a high-intensity focused ultrasound system for directing ultrasound along a beam axis for sonicating a target zone. The target zone is within the imaging zone. The method comprises the step of controlling the magnetic resonance imaging system to acquire the magnetic resonance data using a pulse sequence. The pulse sequence comprises an acoustic radiation force imaging pulse sequence. The acoustic radiation force imaging pulse sequence comprises an excitation pulse. The acoustic radiation force imaging pulse sequence comprises a multi-dimensional gradient pulse applied during the radio-frequency excitation pulse for selectively exciting a region of interest. The region of interest comprises a predetermined volume that encompasses the target zone and at least a portion of the beam axis. The method further comprises the step of controlling the high-intensity focused ultrasound system to sonicate the target zone using the high-intensity focused ultrasound system such that the sonication of the target zone occurs during the acoustic radiation force imaging pulse sequence. The method further comprises the step of reconstructing the radiation force image using the magnetic resonance data.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
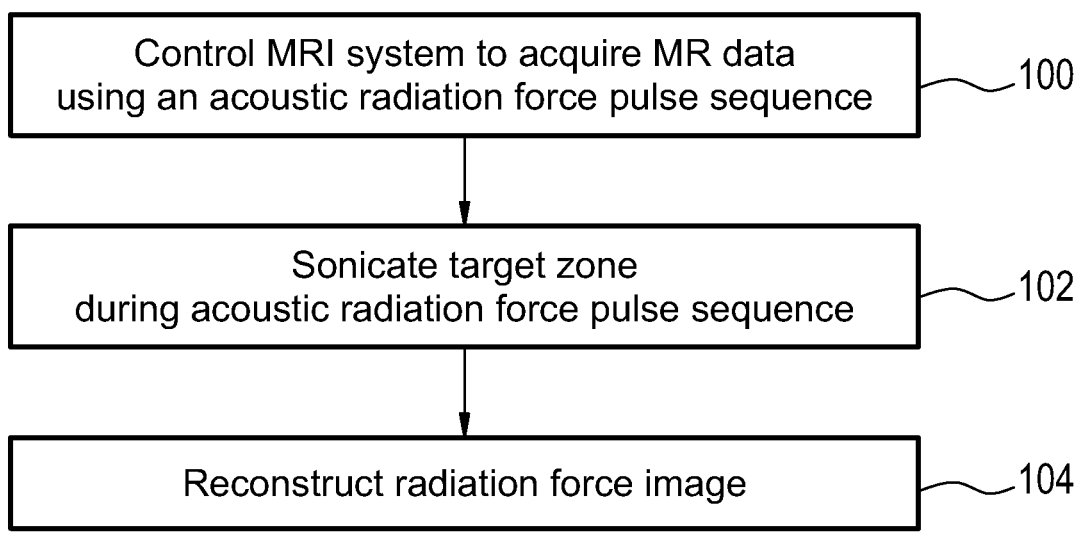
FIG. 1 illustrates a method according to an embodiment of the invention.

FIG. 1 shows a flowchart which illustrates a method according to an embodiment of the invention. First in step 100 a magnetic resonance imaging system is controlled to acquire magnetic resonance data using a pulse sequence. The pulse sequence comprises an acoustic radiation force imaging pulse sequence. The acoustic radiation force imaging pulse sequence comprises an excitation pulse. The acoustic radiation force imaging pulse sequence comprises a multi-dimensional gradient pulse applied during the radio-frequency excitation pulse for selectively exciting the region of interest. The region of interest comprises a predetermined volume that encompasses the target zone and at least a portion of the beam axis. Next in step 102 a high-intensity focused ultrasound system is controlled to sonicate the target zone such that the sonication of the target zone occurs during the acoustic radiation force imaging pulse sequence. Finally in step 104 a radiation force image is reconstructed using the magnetic resonance data. The radiation force image may include one-dimensional data, for instance in the case of using a one-dimensional readout gradient.

Figure 2:
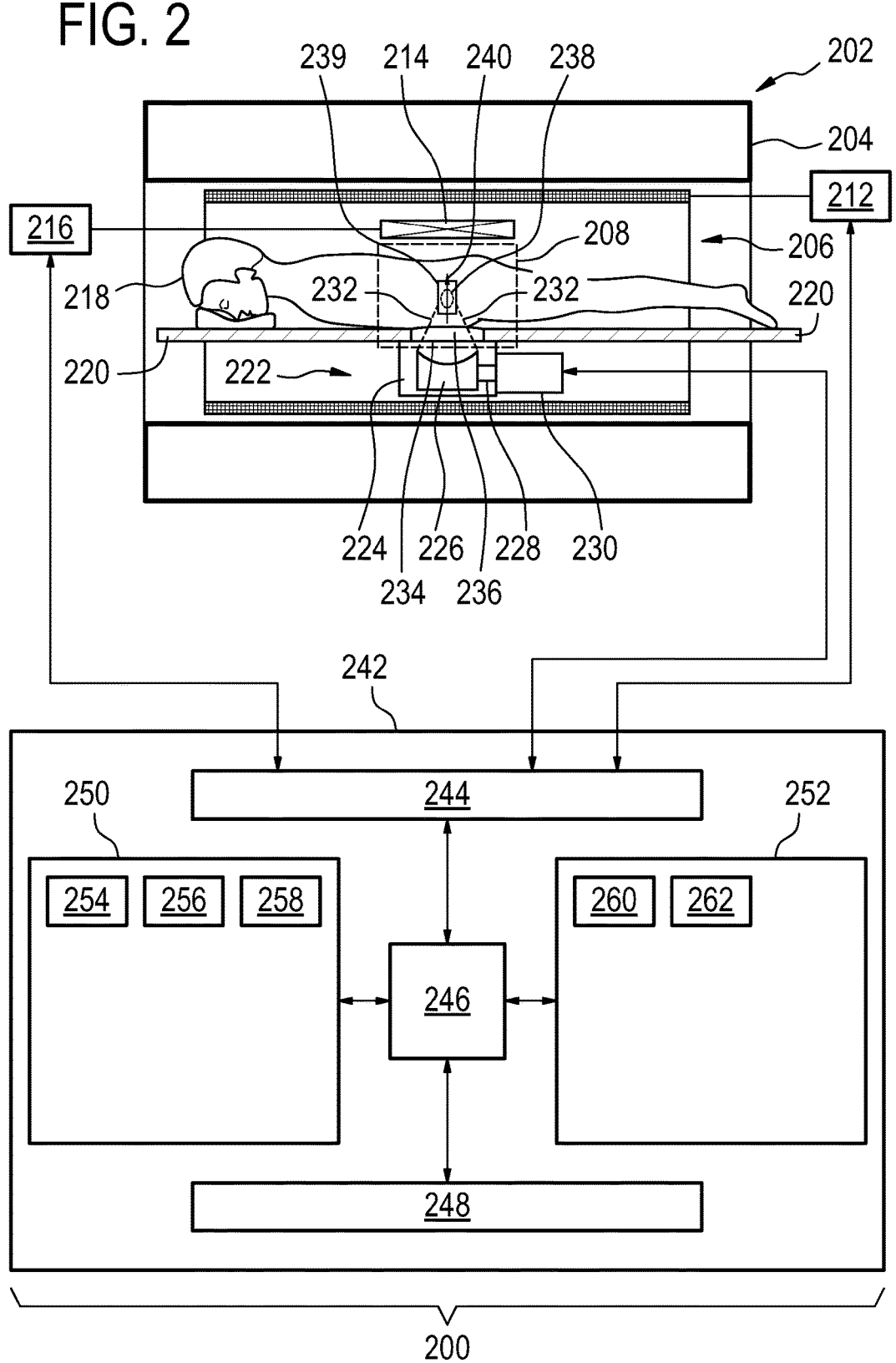
FIG. 2 illustrates a medical apparatus according to an embodiment of the invention.
Figure 3:
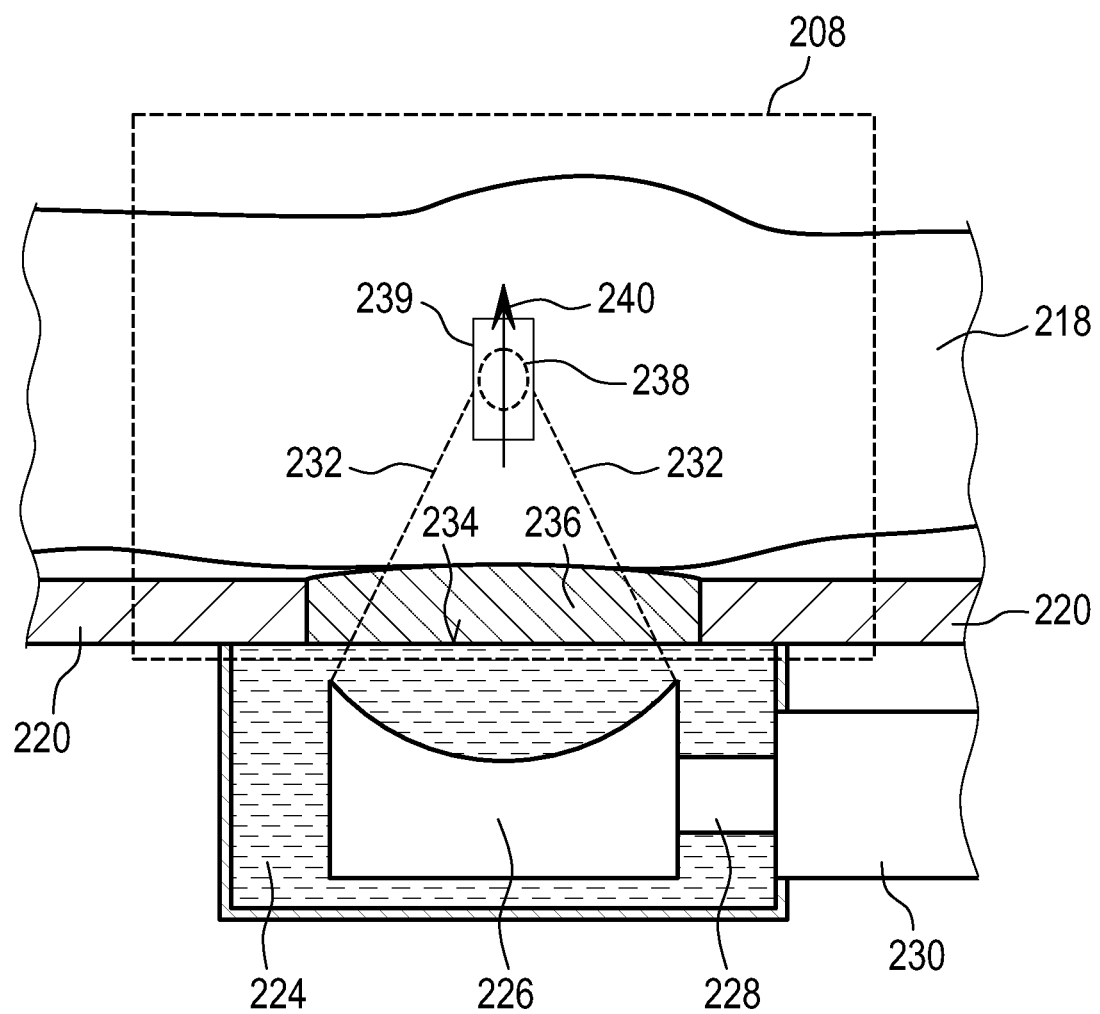
FIG. 3 illustrates a zoomed portion of FIG. 2.

FIGS. 2 and 3 show a medical instrument 200 according to an embodiment of the invention. FIG. 3 shows an enlarged view of a portion of FIG. 2. The medical instrument 200 comprises a magnetic resonance imaging system 202. The magnetic resonance imaging system comprises a magnet 204. The magnet 204 is a cylindrical type superconducting magnet with a bore 206 through the center of it. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 206 of the cylindrical magnet there is an imaging zone 308 where the magnetic field is strong and uniform enough to perform magnetic resonance imaging.

Within the bore 206 of the magnet there is also a set of magnetic field gradient coils 210 which are used for acquisition of magnetic resonance data to spatially encode magnetic spins within the imaging zone 208 of the magnet 204. The magnetic field gradient coils are connected to a magnetic field gradient coil power supply 212. The magnetic field gradient coils 210 are intended to be representative. Typically magnetic field gradient coils contain three separate sets of coils for spatially encoding in three orthogonal spatial directions. A magnetic field gradient power supply 212 supplies current to the magnetic field gradient coils 210. The current supplied to the magnetic field coils is controlled as a function of time and may be ramped or pulsed.

Adjacent to the imaging zone 208 is a radio-frequency coil 214 for manipulating the orientations of magnetic spins within the imaging zone 208 and for receiving radio transmissions from spins also within the imaging zone. The radio-frequency coil may contain multiple coil elements. The radio-frequency coil may also be referred to as a channel or an antenna. The radio-frequency coil 214 is connected to a radio frequency transceiver 216. The radio-frequency coil 214 and radio frequency transceiver 216 may be replaced by separate transmit and receive coils and a separate transmitter and receiver. It is understood that the radio-frequency coil 214 and the radio-frequency transceiver 216 are representative. The radio-frequency coil 214 is intended to also represent a dedicated transmit antenna and a dedicated receive antenna. Likewise the transceiver 216 may also represent a separate transmitter and receivers.

A subject 218 is shown as reposing on a subject support 220 and is located partially within the imaging zone 208. The medical instrument 200 also comprises a high-intensity focused ultrasound system 222. The high-intensity focused ultrasound system comprises a fluid-filled chamber 224. Within the fluid-filled chamber 224 is an ultrasound transducer 226. Although it is not shown in this figure the ultrasound transducer 226 may comprise multiple ultrasound transducer elements each capable of generating an individual beam of ultrasound. This may be used to steer the location of a sonication point 238 electronically by controlling the phase and/or amplitude of alternating electrical current supplied to each of the ultrasound transducer elements. Point 238 represents the adjustable focus of the medical instrument 200.

The ultrasound transducer 226 is connected to a mechanism 228 which allows the ultrasound transducer 226 to be repositioned mechanically. The mechanism 228 is connected to a mechanical actuator 230 which is adapted for actuating the mechanism 228. The mechanical actuator 230 also represents a power supply for supplying electrical power to the ultrasound transducer 226. In some embodiments the power supply may control the phase and/or amplitude of electrical power to individual ultrasound transducer elements. In some embodiments the mechanical actuator/power supply 230 is located outside of the bore 206 of the magnet 204.

The ultrasound transducer 226 generates ultrasound which is shown as following the path 232. The ultrasound 232 goes through the fluid-filled chamber 228 and through an ultrasound window 234. In this embodiment the ultrasound then passes through a gel pad 236. The gel pad 236 is not necessarily present in all embodiments but in this embodiment there is a recess in the subject support 220 for receiving a gel pad 236. The gel pad 236 helps couple ultrasonic power between the transducer 226 and the subject 218. After passing through the gel pad 236 the ultrasound 232 passes through the subject 218 and is focused to a sonication point 238 or target zone. The arrow 240 indicates the beam axis. When ultrasound is applied to the target zone the subject will experience a force in the direction of the arrow 240. The region of interest 239 is indicated by the box 239. It is shown as encompassing the target zone 238 and a portion of the beam axis 240.

The sonication point 238 may be moved through a combination of mechanically positioning the ultrasonic transducer 226 and electronically steering the position of the sonication point 238 to treat the entire target volume 240.

The magnetic field gradient coil power supply 212, the transceiver 216, and the mechanical actuator/power supply 230 of the high-intensity focused ultrasound system 222 are shown as being connected to a hardware interface 244 of computer 242. The computer 242 further comprises a processor 246, a user interface 248, computer storage 250, and computer memory 2. The hardware interface 244 enables the processor 246 to send and receive commands and data in order to control the functioning of the medical instrument 200. The processor 246 is further connected to the user interface 248, the computer storage 250, and the computer memory 252.

The computer storage 250 is shown as containing a pulse sequence 254. The pulse sequence 254 comprises an acoustic radiation force imaging pulse sequence. The pulse sequence may also comprise other types of pulse sequences such as a normal imaging pulse sequence or a thermal imaging pulse sequence. The computer storage 250 is shown as further containing magnetic resonance data 256 that was acquired by the magnetic resonance imaging system 202 using the pulse sequence 254. The computer storage 250 is further shown as containing a radiation force image 258 that was reconstructed from the magnetic resonance data 256.

The computer memory 252 is shown as containing a control module 260. The control module 260 comprises computer-executable code which enables the processor 246 to control the operation and function of the magnetic resonance imaging system 202. For instance the control module 260 may use the pulse sequence 254 to control the magnetic resonance imaging system 202 to acquire the magnetic resonance data 256. The computer memory 252 is shown as further containing a radiation force image reconstruction module 262. The radiation force image reconstruction module 262 contains computer-executable code which enables the processor 246 to reconstruct the radiation force image 258 using the magnetic resonance data 256. The radiation force image reconstruction module 262 may also use data concerning the operation and timing of the high-intensity focused ultrasound system 222 for reconstructing the radiation force image 258. Since the sonication of the target zone 238 is synchronized with the acquisition of the magnetic resonance data 256 it is likely that in some embodiments the high-intensity focused ultrasound system 222 will be gated using the pulse sequence 254.

Figure 4:
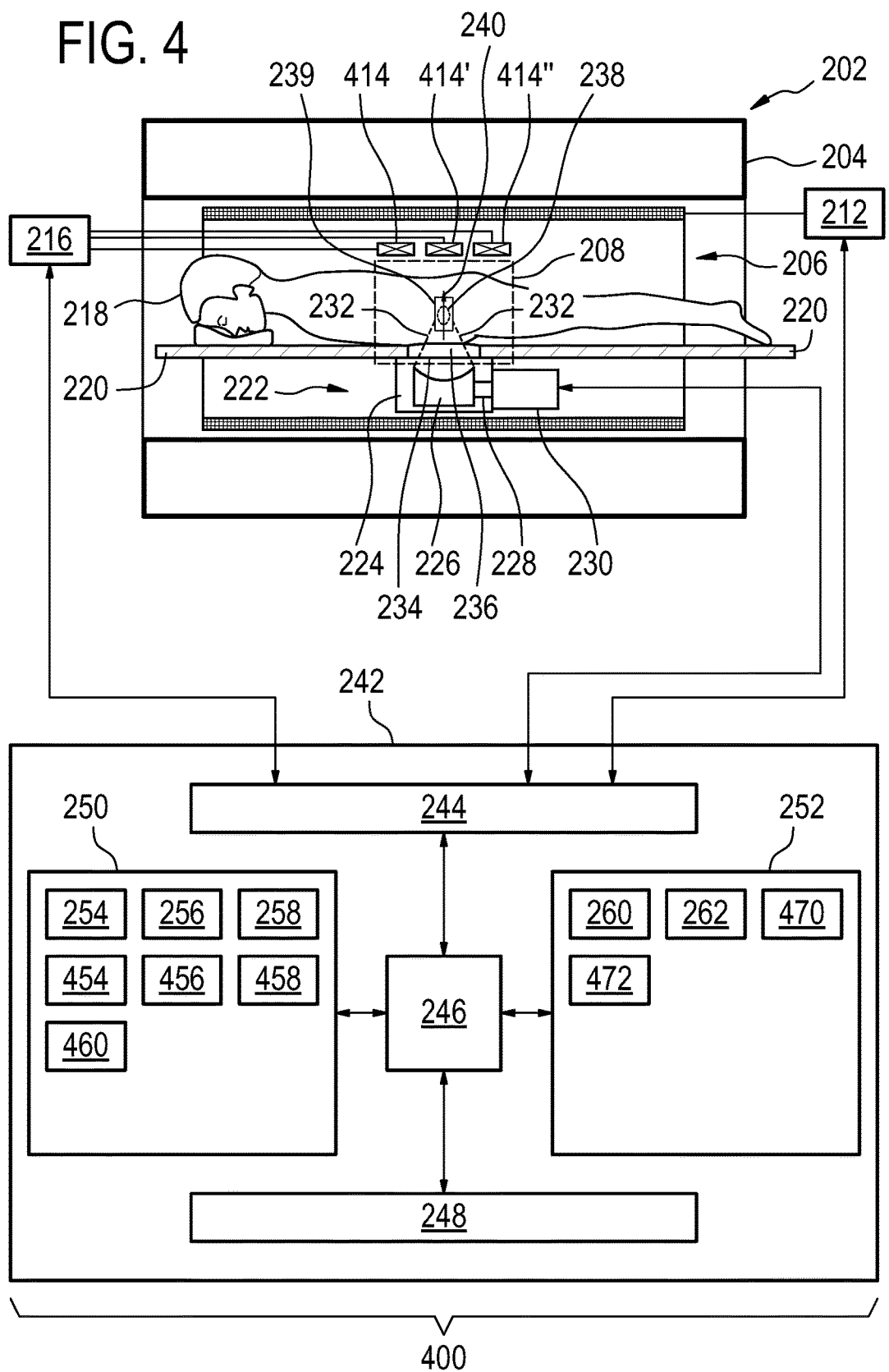
FIG. 4 illustrates a medical apparatus according to a further embodiment of the invention.

FIG. 4 illustrates a medical instrument 400 that is similar to the medical instruments illustrated in FIGS. 2 and 3. In this case there are four radio-frequency coils 414, 414', 414". These are shown as being connected to the transceiver 216. The combination of the transceiver 216 and the radio-frequency coils 414, 414', 414" illustrates a radio-frequency system connected to a multi-element transmit coil. This may be used for shortening the excitation pulse duration or improving the spatial excitation profile of the region of interest.

The computer storage 250 is shown as containing thermal imaging pulse sequence 454. The thermal imaging pulse sequence 454 may be interleaved into the pulse sequence 254. The computer storage 250 is further shown as containing thermal magnetic resonance data 456 that was acquired using the thermal imaging pulse sequence 454. The computer storage 250 is further shown as containing a thermal map 258 that was reconstructed from the thermal magnetic resonance data 456. The computer storage is further shown as containing a treatment plan 460 which specifies the location of the target zone 238. The control module 260 may enable the processor 246 to control the operation and function of the medical instrument 400 using the treatment plan 460.

The computer memory 252 is shown as containing a thermal map reconstruction module 470. The thermal map reconstruction module 470 enables the processor 246 to reconstruct the thermal map 458 from the thermal magnetic resonance data 456. The computer memory 252 is further shown as containing a treatment plan modification module 472. The treatment plan modification module 472 enables the processor 246 to modify the treatment plan 460 using at least the radiation force image 258.

Figure 5:
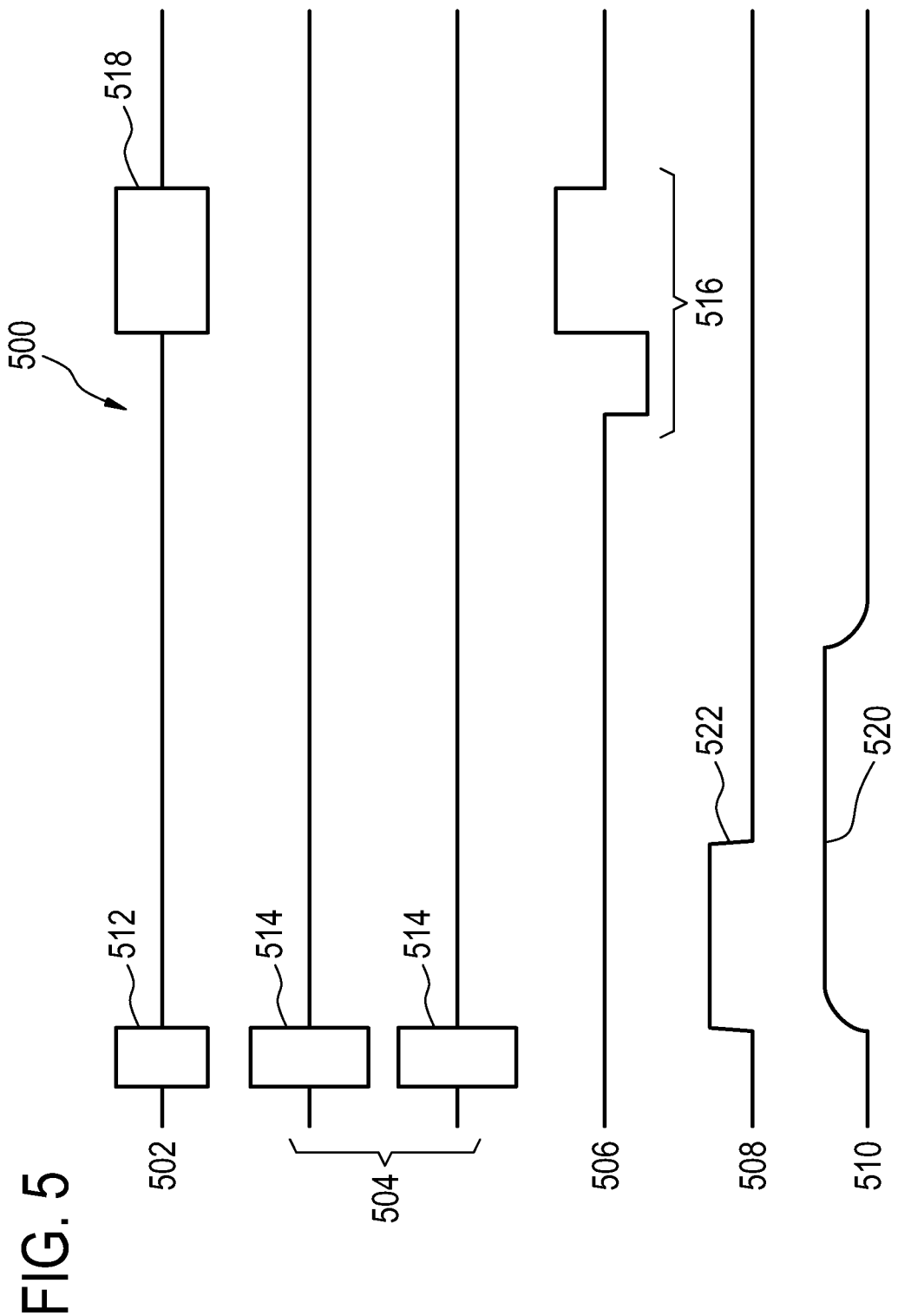
FIG. 5 illustrates an example of an acoustic radiation force imaging pulse sequence.

FIG. 5 illustrates an acoustic radiation force imaging pulse sequence 500 according to an embodiment of the invention. There are several timing lines shown in FIG. 5. The first timing line is 502 which shows the radio-frequency timing line. The two lines marked 504 are the line selection gradient timing lines. The line 506 is the timing line for the readout gradients. Line 508 shows an encoding gradient timing line. Line 510 shows a timing line for the switching of the high-intensity focused ultrasound system. In many instances various actions performed on the lines marked 504, 506 and 508 would in fact be performed by the same gradient coils at different periods of time. It can be seen in the timing diagram first there is a radio-frequency excitation pulse 512 that is indicated on line 502. The box shape indicates an unspecified shape for the radio-frequency pulse. At the same time on the lines marked 504 a multi-dimensional gradient 514 is performed. The shapes of the gradients are also represented as being unspecified by the box shapes. After the radio-frequency excitation 512 is over, the high-intensity focused ultrasound system is switched on. This is indicated by the ultrasound on pulse 520 on line 510. During at least a portion of when the ultrasound is on 520 a spatial encoding gradient pulse 522 is performed. This is indicated on line 508. After the high-intensity focused ultrasound has been turned off a readout gradient pulse 516

Figure 6:
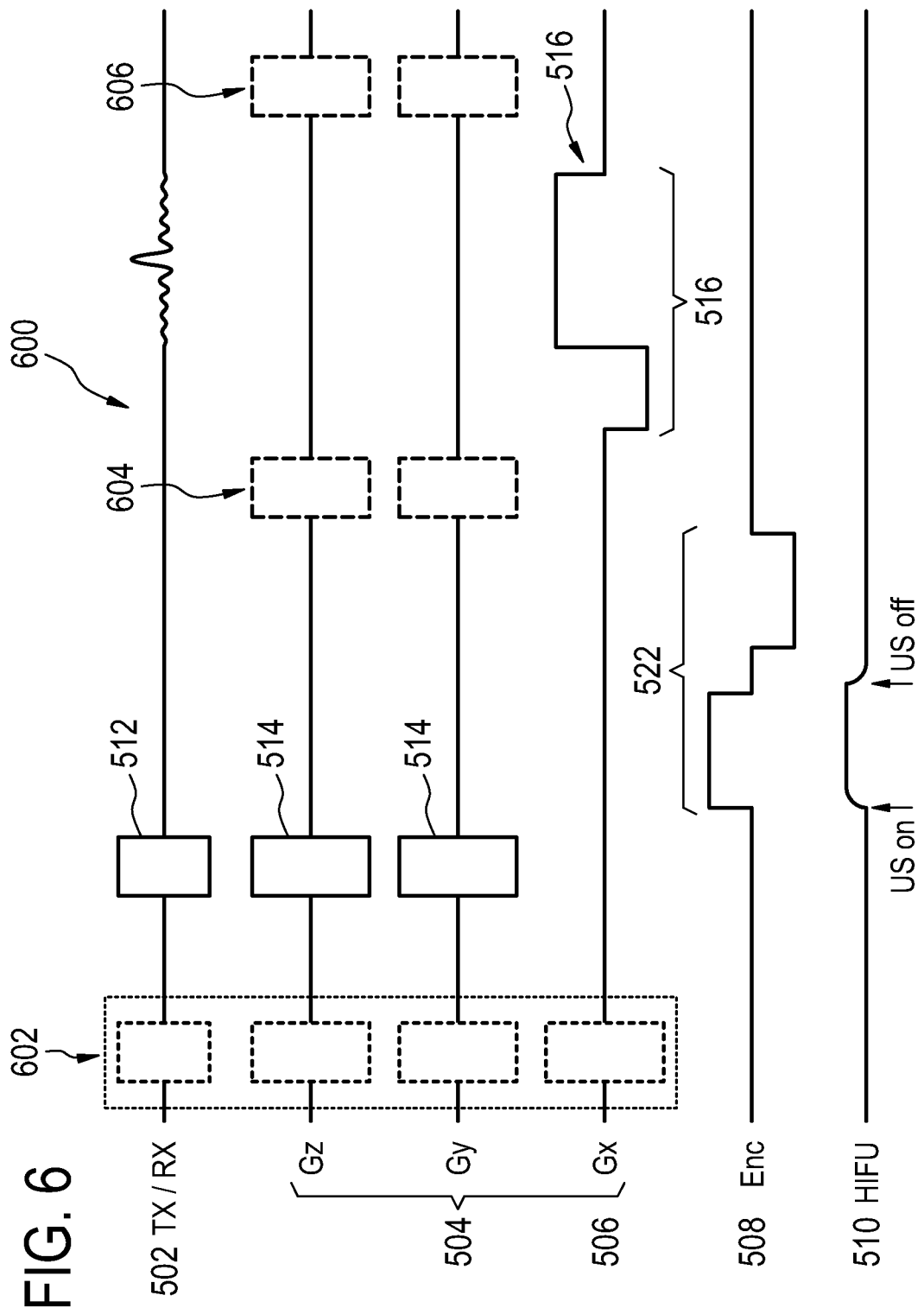
FIG. 6 illustrates a further example of an acoustic radiation force imaging pulse sequence.

FIG. 6 illustrates an alternative acoustic radiation force imaging pulse sequence 600. The pulse sequence 600 is similar to the pulse sequence 500 shown in FIG. 5. In addition an additional set of radio frequency pulse and gradient pulses 602 have been added to perform optional volume suppression using the outer volume suppression technique as is detailed in Wilm et. al. Magnetic resonance in Medicine 57: 625-630 (2007). Optional gradient pulses 604 and 606 are also shown. Gradient pulse 604 is an optional phase encoding gradient which would be needed if generating two- or three-dimensional MR-ARFI images. It is important to bear in mind that the MR-AFRI images may be one-dimensional data, in which case gradient pulse 604 is not necessary. Gradient pulse 606 is an optional refocusing gradient pulse which is needed if reading out more echoes than one for each excitation as is done in EPI and TSE type readouts. Gradient pulse 606 can also be used as a dephasing spoiler gradient for reducing the risk of spurious echoes occurring.

MR-ARFI is the combination of MR acquisition with a mechanical pressure field to measure the in vivo tissue displacement due to the force exerted by the mechanical pressure field. In the context of this ID, the focus will be on MR-ARFI for evaluation of different features related to high-intensity focused ultrasound.

By triggering MR acquisition to the start of a HIFU pulse (continuous several milliseconds in duration), and encoding the displacement via for example bi-polar gradients one can then obtain a displacement map that gives a measure of the acoustic radiation force that in turn correlates with the applied local pressure field.

However, since the HIFU required for ARFI is only applied in short bursts of tens of ms with a duty cycle less than 30%, instead of continuously over tens of seconds the heating is. Also, the acoustic powers required are rather low for ARFI, but do affect the SNR of the displacement maps giving noisy displacement estimates if the power is too low.

The application of MR-ARFI may for example be used to obtain an estimate of the focal spot location without causing any heating or damage to the tissue. This can be useful in itself in acoustically heterogeneous tissues or small structures where the accuracy of the heating location is paramount.

Another application that can also be particularly useful in acoustically complex environments, such as sonicating between the ribs, and aiming for the liver, is to maximize the displacement in the focus thereby maximizing the pressure field for a given applied power. This can be done by altering the phase of individual elements or element clusters one by one until the phase resonance at the focal spot is maximized. Also, one can build in the switching off of elements that do not contribute to the focal spot pressure at all, on the assumption that they are then only being absorbed in the ribs and during ablation would contribute to the heating of the ribs alone. If the rib heating is excessive, then nerve and skin damage may result.

Yet another possible use is the monitoring for changes in tissue structure during sonication. This can for example be used to monitor for onset of cavitation that would cause the local reflection/absorption to be increased. Moreover, for higher acoustic intensities the energy is transferred to higher harmonics that in turn cause a more efficient absorption near the focus. This can be highly desirable, and ARFI can potentially be used to monitor the onset and extent of these non-linearities due to the increased absorption and radiation force that these produce. This would in turn increase the radiation force which can be readily monitored by MR-ARFI. This ARFI monitoring should be done intermittently to thermometry when used for cavitation monitoring during HIFU ablation.

One more identified application is the monitoring of pressure induced drug delivery or gene expression.

However, all of these applications would greatly benefit from rapid MR-ARFI, particularly those applications where ARFI must be done intermittently to thermometry or other monitoring or where the amount of repetitions needed of the ARFI is large as is the case for drive signal optimization. This invention discusses methods with which MR-ARFI can be accelerated to clinically acceptable imaging durations.

Conventionally MR-ARFI uses 2D imaging or in some cases the use of stacked 1D profiles being combined to a 2D image has also been reported. Essentially 2D images are produced.

For some of the more interesting applications of MR-ARFI such as adaptive refocusing, pressure field monitoring, cavitation/non-linearity monitoring the MR-ARFI should preferably be very rapid. This is not so much of a concern for test shots where it is quite acceptable to obtain an image in the matter of some seconds.

However, for adaptive refocusing this scan must be repeated at least 3 times the amount of elements in the transducer that are to have their driving signal modified. 3 repetitions are needed at different driving phases for each element in order to obtain an adequate understanding of the behavior of radiation force vs. phase behavior of that channel. Preferably two images should be made of each driving phase for each channel in order to remove background MR phase noise. If a radiation force image is obtained in 2 s, which would be acceptable for test shot purposes, the repetitions needed for adaptive refocusing quickly causes the scan time to become on the order of an hour. This is of course too long to be clinically useful.

However, since we are interested in maximizing the radiation force we do not necessarily need to make a 2D image of the displacement field after the location of the focus has been determined to be correct in one image.

In one embodiment, a 2D cylindrical excitation pulse is followed by 1D gradient readout pulse. The direction of the cylindrical pencil-beam excitation should be the same as the 1D readout pulse and should coincide with the beam axis of the HIFU field. The MR phase signal in each voxel of that 1D profile should then represent the average radiation force perpendicular to the beam axis that was within the volume excited by the 2D RF pulse. In order for the averaging not to even out the signal too much, the diameter of the pencil beam must be kept as small as possible and coincide with the beam axis of the HIFU. Such an excitation of a reasonable diameter (~5 mm) plus readout can be obtained in 30 ms. This would allow for the adaptive refocusing of a 256 element transducer to be done in less than a minute (3*2*256*30 ms=46 s). However, averaging may be necessary to obtain sufficiently reliable estimates of the radiation force. Although this would at least double the imaging time, the scan time nevertheless remains feasible.

In another embodiment, multi transmit technique may be utilized to decrease the time needed for multi-dimensional encoding of excitation k-space by allowing undersampling or trading this in for improved excitation k-space coverage, in a very analogous way as traditional receive SENSitivity Encoding (SENSE).

In another embodiment, the restricted region of interest that is excited by the multi-dimensional excitation is reconstructed as a 2D image. The restricted field of view excited would then enable less phase encoding steps to be required thereby reducing the scan duration of any conventional 2D imaging technique for ARFI. This may be combined with readout acceleration techniques such as SENSE or Generalized Autocalibrating Partially Parallel Acquisition (GRAPPA) to further reduce the amount of phase encoding steps needed. Using a fast field echo for the imaging sequence in combination with for example a segmented Echo Planar Imaging (EPI) readout would then enable a rapid acquisition in the order of 100-200 ms per image. Reconstruction techniques based on data inheritance or sparse sampling may furthermore be combined with the conventional imaging scans as there is very little change from one image to the next and much of the data may be inherited. Techniques such as image ratio constrained reconstruction and k-t GRAPPA could be used to name a few.

These techniques are also as said applicable for monitoring of cavitation and non-linearities as well as pressure field monitoring, not only for driving phase calibration.

In many applications of the invention the absolute value of the displacement is not important, but instead if there has been any change in the displacement as a result of cavitation or the change in drive phase for example.

Hence, pencil beam excitations may be used to reduce the Field of View (FOV) and gain a very rapid idea of the displacement estimate within the pencil beam. Comparison between subsequent profiles may allow determination of the relationship between transducer element drive signal and radiation force, thereby allowing for adaptive refocusing.

Alternatively this comparison may yield information on the changes in the local pressure field and tissue behavior near the focus that arise from increasing the power level (cavitation/non-linearities).

In a slightly different way, multi transmit techniques and/or traditional receive acceleration techniques may be used to undersample excitation or receive k-space, respectively. Undersampling may be used to reduce the k-space coverage necessary thereby shortening the excitation pulse duration for excitation k-space and reduce the amount of phase-encodings needed in receive k-space, without causing aliasing. Moreover, receive undersampling can be combined with reconstruction techniques that use data inheritance such as k-t GRAPPA, compressed sensing, and image ratio constrained reconstruction.

The imaging techniques outlined above may be combined with motion sensitizing gradients pulses in the beam direction. This then is combined with images obtained with ultrasound active and then repeated with opposite polarity gradients. The resulting data will then allow for a reconstruction of a displacement map with background MR phase removed.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 200 medical instrument
202 magnetic resonance imaging system
204 magnet
206 bore of magnet
208 imaging zone
210 magnetic field gradient coils
212 magnetic field gradient coils power supply
214 radio-frequency coil
216 transceiver
218 subject
220 subject support
222 high intensity focused ultrasound system
224 fluid filled chamber
226 ultrasound transducer
228 mechanism
230 mechanical actuator/power supply
232 path of ultrasound
234 ultrasound window
236 gel pad 238 sonication point or target zone
239 region of interest
240 beam axis
242 computer system
244 hardware interface
246 processor
248 user interface
250 computer storage
252 computer memory
254 pulse sequence
256 magnetic resonance data
258 radiation force image
260 control module
262 radiation force image reconstruction module
414 radio-frequency coil
414' radio-frequency coil
414" radio-frequency coil
454 thermal imaging pulse sequence
456 thermal magnetic resonance data
458 thermal map
460 treatment plan
470 thermal map reconstruction module
472 treatment plan modification module
500 acoustic radiation force imaging pulse sequence
502 radio frequency timing line
504 line selection gradients timing line
506 readout gradients timing line
508 encoding gradient timing line
510 high intensity focused ultrasound timing line
512 excitation pulse
514 multi dimensional gradient
516 readout gradient
518 received radio frequency signal
520 ultrasound on
522 spatial encoding

The invention claimed is:

1. A medical apparatus comprising:
a magnetic resonance imaging system that acquires magnetic resonance data from a subject within an imaging zone;
a high intensity focused ultrasound system that directs ultrasound along a beam axis to sonicate a target zone, wherein the target zone is within the imaging zone;
a processor that controls the medical apparatus;
a memory that stores machine-readable instructions, wherein execution of the instructions causes the processor to:
control the magnetic resonance imaging system to acquire the magnetic resonance data using a pulse sequence, wherein the pulse sequence comprises an acoustic radiation force imaging pulse sequence, wherein the acoustic radiation force imaging pulse sequence comprises a radio frequency excitation pulse, wherein the acoustic radiation force imaging pulse sequence comprises a multi-dimensional gradient pulse applied during the radio frequency excitation pulse for selectively exciting a region of interest, the multi-dimensional gradient pulse being a two-dimensional gradient pulse for exciting the region of interest such that the region of interest has a two-dimensional cross section, wherein the two-dimensional cross section has rotational symmetry with respect to a region-of-interest axis, wherein the region-of-interest axis and the beam axis are coaxial, and wherein the region of interest comprises a predetermined volume that encompasses the target zone and at least a portion of the beam axis, and wherein the acoustic radiation force imaging pulse sequence further comprises a one-dimensional readout gradient pulse aligned with or coinciding with the beam axis;
control the high intensity focused ultrasound system to sonicate the target zone by directing the ultrasound along the beam axis such that the sonication of the target zone occurs during the acoustic radiation force imaging pulse sequence; and
reconstruct a radiation force image using the magnetic resonance data.

2. The medical apparatus of claim 1, wherein the two-dimensional cross section of the region of interest has any one of the following: a circular shape, an elliptical shape, a rectangular shape, and a polygonal shape.

3. The medical apparatus of claim 2, wherein the magnetic resonance imaging system comprises a multi-element transmit coil, wherein the pulse sequence is operable for causing the magnetic resonance imaging system to restrict the region of interest to the predetermined volume using the multi-element transmit coil using the multi-dimensional gradient pulse.

4. The medical apparatus of claim 2, wherein the two-dimensional cross section of the region of interest has the circular shape.

5. The medical apparatus of claim 2, wherein the two-dimensional cross section of the region of interest has the elliptical shape.

6. The medical apparatus of claim 2, wherein the two-dimensional cross section of the region of interest has the rectangular shape.

7. The medical apparatus of claim 2, wherein the two-dimensional cross section of the region of interest has the polygonal shape.

8. The medical apparatus of claim 1, wherein the pulse sequence is any one of the following: a SENSE pulse sequence or a GRAPPA pulse sequence.

9. The medical apparatus of claim 1, wherein the two-dimensional gradient pulse is a bi-polar gradient pulse.

10. The medical apparatus of claim 9, wherein execution of the instructions causes the processor to encode a tissue displacement via bi-polar gradients to obtain a displacement map.

11. The medical apparatus of claim 1, wherein the radio frequency excitation pulse is a single excitation pulse.

12. The medical apparatus of claim 1, wherein the pulse sequence further comprises a displacement encoding gradient pulse, wherein execution of the instructions cause the processor to control the high intensity focused ultrasound system to sonicate the target zone using the high intensity focused ultrasound system such that the sonication of the target zone occurs during at least a portion of the displacement encoding gradient pulse.

13. The medical apparatus of claim 1, wherein the pulse sequence further comprises an outer volume suppression pulse sequence for attenuating magnetic resonance signal outside of the region of interest.

14. The medical apparatus of claim 1, wherein the pulse sequence comprises a thermal imaging pulse sequence for acquiring thermal magnetic resonance data, wherein the thermal imaging pulse sequence is interleaved with the acoustic radiation force imaging pulse sequence, wherein execution of the instructions further causes the processor to:
control the magnetic resonance imaging system to acquire the thermal magnetic resonance data using the thermal imaging pulse sequence;

reconstruct a thermal map using the thermal magnetic resonance data; and display the thermal map and the radiation force image on a display.

15. The medical apparatus of claim 1, where the high intensity focused ultrasound system has an adjustable focus for controlling a location of the target zone, wherein execution of the instructions further causes the processor to:

receive a treatment plan specifying a location of the target zone within the subject;

control the high intensity focused ultrasound system to repeatedly control the adjustable focus at least partially in accordance with the radiation force image and the treatment plan in real time.

16. The medical apparatus of claim 1, wherein the radio frequency excitation pulse comprises a two-dimensional radio frequency excitation pulse.

17. The medical apparatus of claim 16, wherein the two-dimensional radio frequency excitation pulse comprises a two-dimensional cylindrical radio frequency excitation pulse.

18. The medical apparatus of claim 17, wherein the two-dimensional cylindrical radio frequency excitation pulse is followed by the one-dimensional gradient readout pulse, and a direction of a cylindrical pencil-beam excitation of the region of interest is the same as a direction of the one-dimensional gradient readout pulse, the direction coinciding with the beam axis.

19. A computer program product comprising a non-transitory computer readable medium storing machine executable code for execution by a processor that controls a medical apparatus, wherein the medical apparatus comprises a magnetic resonance imaging system that acquires magnetic resonance data from a subject within an imaging zone, wherein the medical apparatus further comprises a high intensity focused ultrasound system that directs ultrasound along a beam axis to sonicate a target zone, wherein the target zone is within the imaging zone, wherein execution of the instructions causes the processor to:

control the magnetic resonance imaging system to acquire the magnetic resonance data using a pulse sequence, wherein the pulse sequence comprises an acoustic radiation force imaging pulse sequence, wherein the acoustic radiation force imaging pulse sequence comprises a radio frequency excitation pulse, wherein the acoustic radiation force imaging pulse sequence comprises a multi-dimensional gradient pulse applied during the radio frequency excitation pulse for selectively exciting a region of interest, the multi-dimensional gradient pulse being a two-dimensional gradient pulse for exciting the region of interest such that the region of interest has a two dimensional cross section, wherein the two-dimensional cross section has rotational symmetry with respect to a region of interest axis, wherein the region of interest axis and the beam axis are coaxial, wherein the region of interest comprises a predetermined volume that encompasses the target zone and at least a portion of the beam axis, and wherein the acoustic radiation force imaging pulse sequence further comprises a one-dimensional readout gradient pulse aligned with or coinciding with the beam axis;

control the high intensity focused ultrasound system to sonicate the target zone by directing the ultrasound along the beam axis such that the sonication of the target zone occurs during the acoustic radiation force imaging pulse sequence; and reconstruct a radiation force image using the magnetic resonance data.

20. A method of operating a medical apparatus, wherein the medical apparatus comprises a magnetic resonance imaging system that acquires magnetic resonance data from a subject within an imaging zone, wherein the medical apparatus further comprises a high intensity focused ultrasound system that directs ultrasound along a beam axis to sonicate a target zone, wherein the target zone is within the imaging zone, wherein the method comprises the steps of:

controlling the magnetic resonance imaging system to acquire the magnetic resonance data using a pulse sequence, wherein the pulse sequence comprises an acoustic radiation force imaging pulse sequence, wherein the acoustic radiation force imaging pulse sequence comprises a two-dimensional cylindrical radio frequency excitation pulse, wherein the acoustic radiation force imaging pulse sequence comprises a multi-dimensional gradient pulse applied during the two-dimensional cylindrical radio frequency excitation pulse for selectively exciting a region of interest, the multi-dimensional gradient pulse being a two-dimensional gradient pulse for exciting the region of interest such that the region of interest has a two dimensional cross section, wherein the two-dimensional cross section has rotational symmetry with respect to a region of interest axis, wherein the region of interest axis and the beam axis are coaxial, wherein the region of interest comprises a predetermined volume that encompasses the target zone and at least a portion of the beam axis, and wherein the acoustic radiation force imaging pulse sequence further comprises a one-dimensional readout gradient pulse aligned with or coinciding with the beam axis;

controlling the high intensity focused ultrasound system to sonicate the target zone such by directing the ultrasound along the beam axis that the sonication of the target zone occurs during the acoustic radiation force imaging pulse sequence; and reconstructing a radiation force image using the magnetic resonance data.

* * * * *